United States Patent [19]
Osawa et al.

[11] Patent Number: 5,824,824
[45] Date of Patent: Oct. 20, 1998

[54] SULFONIUM SALTS AND CHEMICALLY AMPLIFIED POSITIVE RESIST COMPOSITIONS

[75] Inventors: Yoichi Osawa; Satoshi Watanabe; Kaysuya Takemura; Shigehiro Nagura, all of Nakakubiki-gun; Akinobu Tanaka, Fujisawa; Yoshio Kawai, Isehara, all of Japan

[73] Assignees: Shin-Etsu Chemical Co., Ltd.; Nippon Telegraph and Telephone Corp., both of Tokyo, Japan

[21] Appl. No.: 742,323

[22] Filed: Nov. 1, 1996

[30] Foreign Application Priority Data

Nov. 2, 1995 [JP] Japan ................................ 7-309849

[51] Int. Cl.⁶ .................................................. C07C 319/00
[52] U.S. Cl. ........................................... 568/49; 430/270.1
[58] Field of Search ............................. 564/430; 568/49; 430/270.1

[56] References Cited

U.S. PATENT DOCUMENTS

| | | | |
|---|---|---|---|
| 3,929,886 | 12/1975 | Isard et al. | 260/567 |
| 5,084,371 | 1/1992 | Schwalm et al. | 430/270 |
| 5,569,784 | 10/1996 | Watanabe et al. | 564/430 |
| 5,633,409 | 5/1997 | Watanabe et al. | 568/49 |

*Primary Examiner*—Brian M. Burn
*Attorney, Agent, or Firm*—Millen, White, Zelano & Branigan, P.C.

[57] ABSTRACT

The invention provides a novel sulfonium salt having at least one acid labile group attached to a phenyl group in a molecule and a $C_2$–$C_{20}$ alkylsulfonate or arylsulfonate anion whose alkyl or aryl has as a substituent an electron withdrawing group such as fluorine and nitro group. The novel sulfonium salt is effective for increasing the dissolution contrast between exposed and unexposed areas. Upon exposure, it generates a substituted alkyl or arylsulfonic acid which is a weak acid, minimizing the influence of side reaction and deactivation during PEB step. The sulfonium salt is useful in a chemically amplified positive resist composition which lends itself to fine patterning and features high resolution.

9 Claims, No Drawings

SULFONIUM SALTS AND CHEMICALLY AMPLIFIED POSITIVE RESIST COMPOSITIONS

BACKGROUND OF THE INVENTION

1. Field of the Invention

This invention relates to a novel sulfonium salt and a chemically amplified positive resist composition containing the same and suitable for use in fine patterning.

2. Prior Art

As the LSI technology tends toward higher integration and higher speed, further refinement of pattern rules is required. Deep-ultraviolet lithography is regarded promising as the next generation of fine patterning technology. The deep-UV lithography is capable of working on the order of 0.3 to 0.4 μm. If a less light absorbing resist is used, it is possible to form a pattern having a side wall nearly perpendicular to the substrate. Great attention is now paid to the technique of utilizing a high illuminance KrF excimer laser as a deep-UV light source. In order to employ this technique on a mass production scale, a resist material having low light absorption and high sensitivity is desired.

From this point of view, a number of chemically amplified positive working resist materials using acid catalysts were recently developed as disclosed in EP 249139, U.S. Pat. No. 4,491,628 and 5,310,619. These materials have high sensitivity, resolution and dry etching resistance and are promising as resist materials especially suited for deep-UV lithography.

It is known that the function of chemically amplified positive resist materials is largely affected by photoacid generators used therein. Typical photoacid generators are onium salts as shown below.

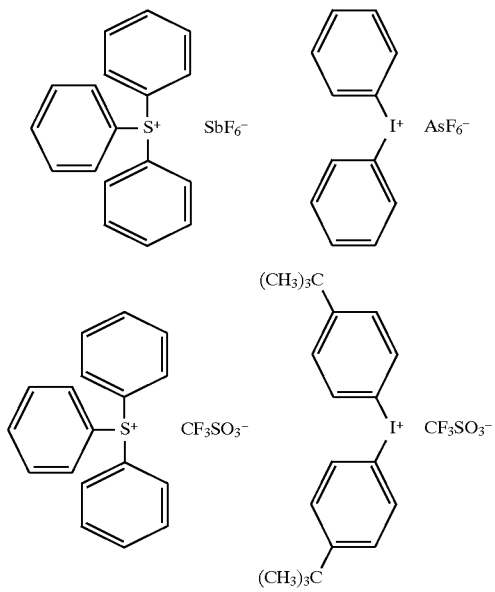

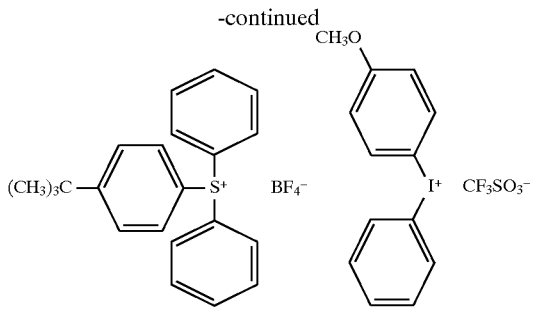

The onium salts themselves are lipophilic. When blended as a resist component, they act to reduce the solubility of the resist material in alkaline aqueous solution and to prevent the resist film from thinning upon development.

However, in exposed areas of positive resist material, photoacid generators absorb actinic radiation to decompose into products which are also lipophilic. The decomposed products reduce the rate of dissolution of the exposed areas in alkaline aqueous solution, failing to provide a high ratio of the alkali dissolution rate of exposed areas to that of unexposed areas (which ratio is known as dissolution contrast).

This problem can be solved by incorporating a tert-butoxycarbonyl group or acid labile group into p-hydroxyphenylsulfonium salts as disclosed in JP-A 26550/1989, 35433/1989, and 12153/1990. Upon exposure to actinic radiation, the salts decompose to generate acids, which help form alkali soluble phenol derivatives, providing an enhanced dissolution contrast.

These tert-butoxycarbonyloxyphenylsulfonium salts, however, lack thermal stability and fail to satisfy the requirement of high resolution. Additionally, they generate strong acids such as metal halide anions and trifluoromethanesulfonic acid. Since the generated acid has high acidity, an acid labile group can be effectively decomposed with a small amount of acid. However, since the amount of acid generated is very small, line patterns would have a T-top profile, that is, patterns become thick at the top if the leave-to-stand or delay time from exposure to post-exposure baking (PEB) is extended. Patterns tend to be readily affected by contamination with air-borne basic substance.

Light exposure generates acid at the resist surface which reacts with air-borne basic substance and is thereby deactivated. As the delay time until PEB is extended, more acid is deactivated and accordingly, decomposition of acid labile groups is more unlikely to occur. As one solution, it is known from JP-A 232706/1993 and 249683/1993 to add a basic compound in a resist material for suppressing the influence of air-borne basic substance. According to our follow-up test, the basic compound used therein is little taken into the resist film due to volatilization, less compatible with resist components, and unevenly dispersible in a resist film. Thus the basic compound cannot achieve its advantages in a reproducible manner and causes a reducer of resolving power.

It is also reported in Proc. SPIE, 2195, 74–83 (1994) that strong acids such as trifluoromethanesulfonic acid resulting from photolysis reaction give rise to undesirable side reaction during PEB step involving decomposition of a tert-butoxycarbonyloxyphenyl group or acid labile group, forming a by-product having a hydroxyphenyl group tert-butylated at the o-position which causes a reducer of alkali solubility.

In the copending application based on Japanese Patent Application No. 309847/1995 assigned to the same assignee as the present invention, there is proposed a novel sulfonium salt which generates an unsubstituted alkylsulfonic acid which is weaker than conventional trifluoromethanesulfonic acid. The pattern configuration changes only a little even when the leave-to-stand time from exposure to post-exposure baking (PEB) is extended. There can still occur a problem that the weak acid would cause the acid labile group to be decomposed to an insufficient extent, less efficient decomposition of an acid labile group requires more acid, and a reducer of sensitivity requires an extended exposure time.

SUMMARY OF THE INVENTION

Therefore, an object of the present invention is to provide a novel sulfonium salt suitable for use in a chemically amplified positive resist composition having sufficiently high resolution to comply with a fine patterning technique. Another an object of the present invention is to provide a chemically amplified positive resist composition containing the novel sulfonium salt.

According to the present invention, there is provided a novel sulfonium salt of the following general formula (1):

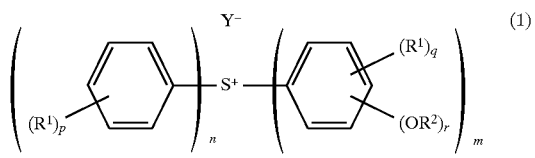

wherein $R^1$ is an alkyl, alkoxy or dialkylamino group, the groups represented by $R^1$ may be the same or different, $OR^2$ is an acid labile group, Y is a normal, branched or cyclic alkylsulfonate having 2 to 20 carbon atoms or arylsulfonate wherein the alkyl group of the alkylsulfonate has at least one hydrogen atom attached to a carbon atom at β-position or subsequent position which is replaced by an electron withdrawing group, the aryl group of the arylsulfonate has at least one hydrogen atom of its benzene ring which is replaced by an electron withdrawing group, letter n is an integer of 0 to 2, m is an integer of 1 to 3, the sum of n and m is equal to 3, r is an integer of 1 to 5, p is an integer of 0 to 5, q is an integer of 0 to 4, the sum of q and r is an integer of 1 to 5.

Using the sulfonium salt of formula (1) as a resist component, there is obtained a chemically amplified positive resist composition which has sufficiently high resolution to comply with a fine patterning technique and is especially effective with deep-UV lithography.

The following advantages are obtainable where the sulfonium salt of formula (1) is used as one component of a chemically amplified positive resist composition. Although the sulfonium salt itself has low alkali solubility, it is decomposed to generate an acid upon exposure to actinic radiation. This acid, combined with a water content in the resist material and the post-exposure bake (PEB), serves to effectively decompose the acid labile group to form a phenol position having high alkali solubility or a carboxylic acid position having high alkali solubility where the acid labile group is a tertiary carboxylate group such as tert-butoxycarbonylmethyloxy group, providing a higher dissolution contrast. Also, those sulfonium salts wherein an oxygen atom is introduced at the 3-position of a phenyl group to prevent the sulfonium salt from assuming a resonance structure between oxygen and sulfur atoms as found in 4-substituted ones, that is, those sulfonium salts having an acid labile group introduced at the 3-position can suppress light absorption at about 250 nm equally to unsubstituted salts, resulting in a resist material having a high transmittance.

Moreover, the acid generated upon exposure to actinic radiation is neither a strong acid like conventional trifluoromethanesulfonic acid nor a relatively weak alkylsulfonic acid, but a substituted alkyl or arylsulfonic acid having an intermediate acid strength. This not only. minimizes the side reaction associated with strong acids and the influence of deactivation of the once generated acid by air-borne basic substance at the resist film surface, but also eliminates insufficient decomposition of an acid labile group as occurring with the use of weak acid like alkylsulfonic acids. Satisfactory sensitivity is ensured.

Therefore, the sulfonium salt of formula (1) performs well as a photoacid generator for a chemically amplified positive resist composition. Owing to the acid labile group in the sulfonium salt of formula (1), the resist composition will form a resist pattern having a high dissolution contrast, high resolution and a wide range of focal depth.

DETAILED DESCRIPTION OF THE INVENTION

In a first aspect, the present invention provides a novel sulfonium salt having at least one acid labile group attached to a phenyl group in a molecule and a normal, branched or cyclic substituted alkylsulfonate having 2 to 20 carbon atoms or substituted arylsulfonate. The sulfonium salt is represented by the following general formula (1):

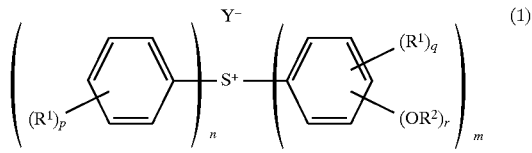

wherein $R^1$ is an alkyl, alkoxy or dialkylamino group, the groups represented by $R^1$ may be the same or different, $OR^2$ is an acid labile group, Y is a normal, branched or cyclic alkylsulfonate having 2 to 20 carbon atoms or arylsulfonate wherein the alkyl group of the alkylsulfonate has at least one hydrogen atom attached to a carbon atom at β-position or subsequent position which is replaced by an electron withdrawing group such as fluorine and nitro group, the aryl group of the arylsulfonate has at least one hydrogen atom of its benzene ring which is replaced by an electron withdrawing group such as fluorine and nitro group, letter n is an integer of 0 to 2, m is an integer of 1 to 3, the sum of n and m is equal to 3, r is an integer of 1 to 5, p is an integer of 0 to 5, q is an integer of 0 to 4, the sum of q and r is an integer of 1 to 5.

Substituents in formula (1) are described in detail. $R^1$ is an alkyl, alkoxy or dialkylamino group. Preferred alkyl groups are those having 1 to 8 carbon atoms such as methyl, ethyl, propyl, isopropyl, n-butyl, sec-butyl, tert-butyl, hexyl, and cyclohexyl groups, with the methyl, ethyl, isopropyl, and tert-butyl groups being especially preferred. Preferred alkoxy groups are those having 1 to 8 carbon atoms such as methoxy, ethoxy, propoxy, isopropoxy, n-butoxy, sec-butoxy, hexyloxy, and cyclohexyloxy groups, with the methoxy, ethoxy, and isopropoxy groups being especially preferred. Preferred dialkylamino groups are those having an alkyl group of 1 to 4 carbon atoms such as dimethylamino, diethylamino and dipropylamino groups, with the dimethylamino group being especially preferred.

OR$^2$ is an acid labile group. Examples of the acid labile group include tertiary alkoxy groups such as tert-butoxy; carbonate groups such as tert-butoxycarbonyloxy; tertiary carboxylate groups such as tert-butoxycarbonylmethyloxy; trialkylsilyloxy groups such as trimethylsilyloxy, triethylsilyloxy, and tert-butyldimethylsilyloxy; and acetal or ketal groups such as tetrahydrofuranyloxy, tetrahydropyranyloxy, 2-methoxytetrahydropyranyloxy, methoxymethyloxy, 1-ethoxyethoxy, 1-propoxyethoxy, 1-n-butoxyethoxy, 1-iso-butoxyethoxy, 1-sec-butoxyethoxy, 1-tert-butoxyethoxy, 1-amyloxyethoxy, 1-ethoxy-1-methylethoxy, 1-propoxy-1-methylethoxy, 1-n-butoxy-1-methylethoxy, 1-isobutoxy-1-methylethoxy, 1-sec-butoxy-1-methylethoxy, 1-tert-butoxy-1-methylethoxy, and 1-amyloxy-1-methylethoxy groups.

Y is a normal, branched or cyclic substituted alkylsulfonate having 2 to 20 carbon atoms or substituted arylsulfonate. The substituted alkyl group is one wherein at least one hydrogen atom attached to a carbon atom at β-position or subsequent position of the alkyl group is replaced by an electron withdrawing group. The substituted aryl group is one wherein at least one hydrogen atom of its benzene ring is replaced by an electron withdrawing group. The alkyl group includes ethyl, propyl, butyl, hexyl and octyl groups. The aryl group includes phenyl, naphthyl, and alkyl-substituted phenyl groups. Examples of the electron withdrawing group include fluorine, nitro group, and cyano group. The electron withdrawing group is attached to a carbon atom of alkyl or aryl at β- or subsequent position.

More illustratively, preferred examples of the substituted alkylsulfonate include 2,2,2-trifluoroethyl-sulfonate, 1H,1H-heptafluoro-1-butylsulfonate, 1H,1H-perfluoro-1-heptylsulfonate, 1H,1H-perfluoro-1-dodecyl-sulfonate, 2-nitroethanesulfonate, 1-nitropropane-2-sulfonate, and 2-nitropropane-1-sulfonate. Preferred examples of the substituted arylsulfonate include penta-fluorobenzenesulfonate, 4-fluorobenzenesulfonate, 2-, 3- or 4-nitrobenzenesulfonate, and 2,4-dinitrobenzenesulfonate.

Where a novel sulfonium salt having a substituted alkyl- or aryl-sulfonate, which is a weaker acid than trifluoromethanesulfonic acid, as a counter anion (Y$^-$) is used as one component of a resist composition, that weak acid anion has the advantage that the influence of deactivation of an acid by air-borne basic substance on the resist film surface is minimized, restraining formation of a difficultly soluble surface layer. The sulfonium salt has satisfactory PED (post-exposure delay) stability, solves the problem of a difficultly soluble surface layer causing a T-top profile, which is known as a PED problem, and provides higher sensitivity. Another advantage is that the acid diffusion length in a resist after exposure can be set by a choice of an anion species.

Examples of the sulfonium salt of formula (1) are given below. The sulfonium salts having an acid labile group at the 4-position of a phenyl group are first exemplified. Examples of the sulfonium salt wherein the acid labile group is a tert-butoxy group include (4-tert-butoxyphenyl) diphenylsulfonium 2,2,2-trifluoroethanesulfonate, (4-tert-butoxyphenyl)diphenylsulfonium pentafluorobenzenesulfonate, (4-tert-butoxyphenyl) diphenylsulfonium 1H,1H-heptafluoro-1-butanesulfonate, bis(4-tert-butoxyphenyl)phenylsulfonium 2,2,2-trifluoroethanesulfonate, tris(4-tert-butoxy-phenyl) sulfonium 2,2,2-trifluoroethanesulfonate, tris(4-tert-butoxyphenyl)sulfonium pentafluorobenzenesulfonate, tris (4-tert-butoxyphenyl)sulfonium 4-fluorobenzenesulfonate, (4-tert-butoxyphenyl)bis(4-dimethylaminophenyl) sulfonium 2,2,2-trifluoroethanesulfonate, and (4-tert-butoxyphenyl)bis(4-dimethylaminophenyl)sulfonium pentafluorobenzenesulfonate.

Examples of the sulfonium salt wherein the acid labile group is a tert-butoxycarbonyloxy group include (4-tert-butoxycarbonyloxyphenyl)diphenylsulfonium 2,2,2-trifluoro-ethanesulfonate, (4-tert-butoxycarbonyloxyphenyl) diphenylsulfonium pentafluorobenzenesulfonate, bis(4-tert-butoxycarbonyloxyphenyl)phenylsulfonium 2,2,2-trifluoroethanesulfonate, tris(4-tert-butoxycarbonyloxyphenyl)sulfonium 2,2,2-trifluoroethanesulfonate, tris(4-tert-butoxycarbonyloxyphenyl)sulfonium pentafluorobenzenesulfonate, (4-tert-butoxycarbonyloxyphenyl)bis(4-dimethylamin ophenyl) sulfonium 2,2,2-trifluoroethanesulfonate, and (4-tert-butoxycarbonyloxyphenyl)bis(4-dimethylaminophenyl) sulfonium 1H,lH-heptafluoro-1-butanesulfonate.

Examples of the sulfonium salt wherein the acid labile group is a tert-butoxycarbonylmethyloxy group include (4-tert-butoxycarbonylmethyloxyphenyl)diphenylsulfonium 2,2,2-trifluoroethanesulfonate, bis(4-tert-butoxycarbonylmethyloxyphenyl)phenylsulfonium pentafluorobenzenesulfonate, tris(4-tert-butoxycarbonylmethyloxyphenyl)sulfonium 1H,1H-heptafluoro-1-butanesulfonate, (4-tert-butoxycarbonylmethyloxyphenyl)bis(4-dimethylaminophenyl)sulfonium 2,2,2-trifluoroethanesulfonate, and (4-tert-butoxycarbonylmethyloxyphenyl)bis(4-dimethylaminophenyl)sulfonium pentafluorobenzenesulfonate.

Examples of the sulfonium salt wherein the acid labile group is an acetal or ketal group include those having a tetrahydropyranyl group, such as (4-(2-tetrahydropyranyl) oxyphenyl)diphenylsulfonium 2,2,2-trifluoroethanesulfonate, bis(4-(2-tetrahydropyranyl) oxyphenyl)phenylsulfonium pentafluorobenzenesulfonate, tris(4-(2-tetrahydropyranyl)oxyphenyl)sulfonium 2,2,2-trifluoroethanesulfonate, tris(4-(2-tetrahydropyranyl) oxyphenyl)sulfonium pentafluorobenzenesulfonate, and (4-(2-tetrahydropyranyl)oxyphenyl)bis(4-dimethylaminophenyl)sulfonium 2,2,2-trifluoroethanesulfonate;

those having a tetrahydrofuranyl group, such as (4-(2-tetrahydrofuranyl)oxyphenyl)diphenylsulfonium pentafluorobenzenesulfonate, bis(4-(2-tetrahydrofuranyl) oxyphenyl)phenylsulfonium 2,2,2-trifluoroethanesulfonate, tris(4-(2-tetrahydrofuranyl)oxyphenyl)sulfonium 2,2,2-trifluoroethanesulfonate, tris(4-(2-tetrahydrofuranyl) oxyphenyl)sulfonium 4-fluorobenzenesulfonate, and (4-(2-tetrahydrofuranyl)oxyphenyl)bis(4-dimethylaminophenyl) sulfonium 2,2,2-trifluoroethanesulfonate; and those having an ethoxyethyl group, such as (4-ethoxy-ethyloxyphenyl)diphenylsulfonium pentafluorobenzenesulfonate, bis(4-ethoxyethyloxyphenyl) phenylsulfonium 2,2,2-trifluoroethanesulfonate, tris(4-ethoxyethyloxyphenyl)sulfonium 2,2,2-trifluoroethanesulfonate, tris(4-ethoxyethyloxyphenyl) sulfonium 4-fluorobenzenesulfonate, and (4-ethoxyethyloxyphenyl)bis(4-dimethylaminophenyl) sulfonium 2,2,2-trifluoroethanesulfonate.

Examples of the sulfonium salt wherein the acid labile group is a trialkylsilyloxy group include 4-trimethylsilyloxyphenyl)diphenylsulfonium 2,2,2-trifluoroethanesulfonate, bis(4-triethylsilyloxyphenyl)phenylsulfonium 4-fluorobenzenesulfonate, tris(4-trimethylsilyloxyphenyl)sulfonium 2,2,2-trifluoroethanesulfonate, and tris(4-triethylsilyloxyphenyl) sulfonium pentafluorobenzenesulfonate.

Next, the sulfonium salts having an acid labile group at the 3-position are described. Examples of the sulfonium salt wherein the acid labile group is a tert-butoxy group include (3-tert-butoxyphenyl)diphenylsulfonium 2,2,2-trifluoroethanesulfonate, (3-tert-butoxyphenyl)diphenylsulfonium pentafluorobenzenesulfonate, (3-tert-butoxyphenyl)diphenylsulfonium 1H,1H-heptafluoro-l-butanesulfonate, bis(3-tert-butoxyphenyl)phenylsulfonium 2,2,2-trifluoroethanesulfonate, tris(3-tert-butoxyphenyl) sulfonium 2,2,2-trifluoroethanesulfonate, tris(3-tert-butoxyphenyl)sulfonium pentafluorobenzenesulfonate, tris(3-tert-butoxyphenyl)sulfonium 4-fluorobenzenesulfonate, (3-tert-butoxyphenyl)bis(4-dimethylaminophenyl)sulfonium 2,2,2-trifluoroethanesulfonate, and (3-tert-butoxyphenyl)bis(4-dimethylaminophenyl)sulfonium pentafluorobenzenesulfonate.

Examples of the sulfonium salt wherein the acid labile group is a tert-butoxycarbonyloxy group include (3-tert-butoxycarbonyloxyphenyl)diphenylsulfonium 2,2,2-trifluoroethanesulfonate, (3-tert-butoxycarbonyloxyphenyl)diphenylsulfonium pentafluorobenzenesulfonate, bis(3-tert-butoxycarbonyloxyphenyl)phenylsulfonium 2,2,2-trifluoroethanesulfonate, tris(3-tert-butoxycarbonyloxyphenyl)sulfonium 2,2,2-trifluoroethanesulfonate, tris(3-tert-butoxycarbonyloxyphenyl)sulfonium pentafluorobenzenesulfonate, (3-tert-butoxycarbonyloxyphenyl)bis(4-dimethylamin ophenyl)sulfonium 2,2,2-trifluoroethanesulfonate, and (3-tert-butoxycarbonyloxyphenyl)bis(4-dimethylamin ophenyl)sulfonium 1H,lH-heptafluoro-1-butanesulfonate.

Examples of the sulfonium salt wherein the acid labile group is a tert-butoxycarbonylmethyloxy group include (3-tert-butoxycarbonylmethyloxyphenyl)diphenylsulfonium 2,2,2-trifluoroethanesulfonate, bis(3-tert-butoxycarbonylmethyloxyphenyl)phenylsulfonium pentafluorobenzenesulfonate, tris(3-tert-butoxycarbonylmethyloxyphenyl)sulfonium 1H,1H-heptafluoro-1-butanesulfonate, (3-tert-butoxycarbonylmethyloxyphenyl)bis(4-dimethylaminophenyl)sulfonium 2,2,2-trifluoroethanesulfonate, and (3-tert-butoxycarbonylmethyloxyphenyl)bis(4-dimethylaminophenyl)sulfonium pentafluorobenzenesulfonate.

Examples of the sulfonium salt wherein the acid labile group is an acetal or ketal group include those having a tetrahydropyranyl group, such as (3-(2-tetrahydropyranyl)oxyphenyl)diphenylsulfonium 2,2,2-trifluoroethanesulfonate, bis(3-(2-tetrahydropyranyl)oxyphenyl)phenylsulfonium pentafluorobenzenesulfonate, tris(3-(2-tetrahydropyranyl)oxyphenyl)sulfonium 2,2,2-trifluoroethanesulfonate, tris(3-(2tetrahydropyranyl)oxyphenyl)sulfonium pentafluorobenzenesulfonate, and (3-(2-tetrahydropyranyl)oxyphenyl)bis(4-dimethylaminophenyl)sulfonium 2,2,2-trifluoroethanesulfonate;

those having a tetrahydrofuranyl group, such as (3-(2-tetrahydrofuranyl)oxyphenyl)diphenylsulfonium pentafluorobenzenesulfonate, bis(3-(2-tetrahydrofuranyl)oxyphenyl)phenylsulfonium 2,2,2-trifluoroethanesulfonate, tris(3-(2-tetrahydrofuranyl)oxyphenyl)sulfonium 2,2,2-trifluoroethanesulfonate, tris(3-(2-tetrahydrofuranyl)oxyphenyl)sulfonium 4-fluorobenzenesulfonate, and (3-(2-tetrahydrofuranyl)oxyphenyl)bis(4-dimethylaminophenyl)sulfonium 2,2,2-trifluoroethanesulfonate; and those having an ethoxyethyl group, such as (3-ethoxyethyloxyphenyl)diphenylsulfonium pentafluorobenzenesulfonate, bis(3-ethoxyethyloxyphenyl)phenylsulfonium 2,2,2-trifluoroethanesulfonate, tris(3-ethoxyethyloxyphenyl)sulfonium 2,2,2-trifluoroethanesulfonate, tris(3-ethoxyethyloxyphenyl)sulfonium 4-fluorobenzenesulfonate, and (3-ethoxyethyloxyphenyl)bis(4-dimethylaminophenyl)sulfonium 2,2,2-trifluoroethanesulfonate.

Examples of the sulfonium salt wherein the acid labile group is a trialkylsilyloxy group include (3-trimethylsilyloxyphenyl)diphenylsulfonium 2,2,2-trifluoroethanesulfonate, bis(3-triethylsilyloxyphenyl)phenylsulfonium 4-fluorobenzenesulfonate, tris(3-trimethylsilyloxyphenyl)sulfonium 2,2,2-trifluoroethanesulfonate, tris(3-triethylsilyloxyphenyl)sulfonium pentafluorobenzenesulfonate.

Although only the sulfonium salts having an acid labile group at the 4 or 3-position of a phenyl group have been illustrated, a sulfonium salt consisting of 3- and 4-substituted ones in a ratio of 2:1 can be synthesized using bis(3-tert-butoxyphenyl) sulfoxide (2d) and 4-tert-butoxyphenyl Grignard reagent (4) as starting reactants as will be described later. Also, a sulfonium salt consisting of 3- and 4-substituted ones in a ratio of 1:2 can be synthesized using bis(4-tert-butoxyphenyl) sulfoxide (2b) and 3-tert-butoxyphenyl Grignard reagent (4) as starting reactants.

The sulfonium salts of formula (1) according to the invention can be synthesized in accordance with the following route. First of all, a 3 or 4-halogenated-tert-butoxybenzene which can be prepared by a well-known method (see J. Holcombe and T. Livinghouse, J. Org. Chem., 111–115, 51 (1986)) is reacted with magnesium in THF in a conventional manner, obtaining a tert-butoxyphenyl Grignard reagent of the general formula (4). Separately, a diaryl sulfoxide of the general formula (2) is reacted with a trialkylsilyl chloride or bromide of the general formula (3) in an organic solvent. The reaction product is reacted with the Grignard reagent of formula (4) to synthesize a sulfonium salt of the general formula (5) having a tert-butoxyphenyl group as an acid labile group and possessing a chloride or bromide ion as an anion. Further, the chloride or bromide ion of the sulfonium salt of formula (5) is reacted with lead carbonate and an alkyl- or arylsulfonic acid of the general formula (6) in methanol to effect anion exchange whereby the chloride or bromide ion is removed as lead chloride or lead bromide. There is obtained a sulfonium salt of formula (1a) having a substituted alkyl- or aryl-sulfonate anion and a tert-butoxyphenyl group. The process for anion exchange may be done in accordance with F. Marshall, J. Am. Chem. Soc., 342–351, 81 (1959).

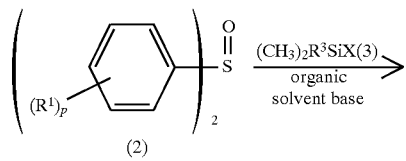

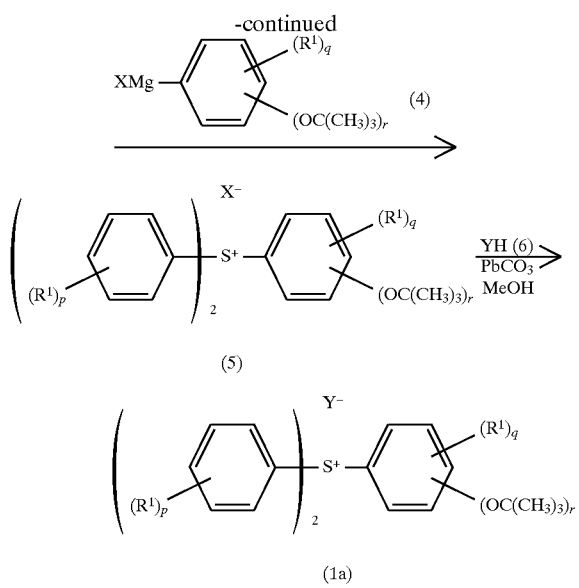

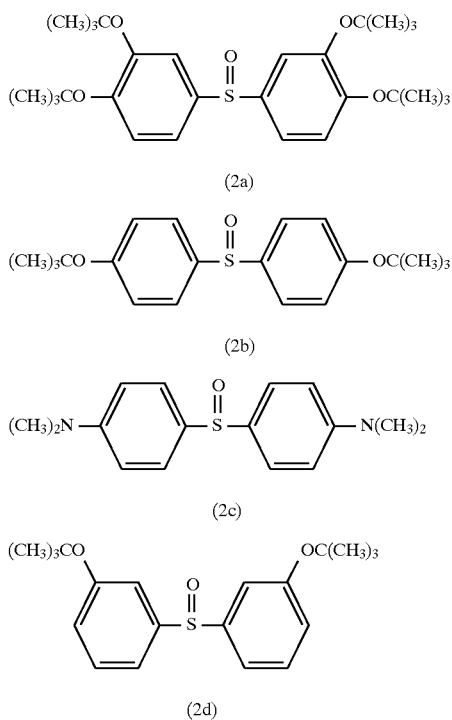

In the formulae, $R^1$, Y, p, q, and r are as defined above, and X is a bromine or chlorine atom.

$R^3$ is a linear or branched alkyl group having 1 to 4 carbon atoms.

The sulfoxide of formula (2) is desirably selected from diphenyl sulfoxide, bis(3,4-di-tert-butoxyphenyl) sulfoxide of formula (2a), bis(4-tert-butoxyphenyl) sulfoxide of formula (2b), bis(4-dimethylaminophenyl) sulfoxide of formula (2c), and bis(3-tert-butoxyphenyl) sulfoxide of formula (2d), all the formulae being shown below. These sulfoxides can be prepared by reacting the corresponding Grignard reagent with thionyl chloride as shown in JPA 7-215930.

Preferred examples of trialkylsilyl chloride or bromide represented by the above formula (3) include trimethylsilyl chloride, trimethylsilyl bromide, tert-butyldimethylsilyl chloride, tert-butyldimethylsilyl bromide, ethyldimethylsilyl chloride and ethyldimethylsilyl bromide.

According to the invention, novel sulfonium salts having one or three tert-butoxyphenyl groups can be synthesized using the above-mentioned sulfoxides as a starting material. Alternatively, a novel sulfonium salt of formula (1b) having a substituted alkyl- or aryl-sulfonate anion and two tert-butoxyphenyl groups can be synthesized by reacting the bis(tert-butoxyphenyl) sulfoxide of formula (2b) or (2d) with an aryl Grignard reagent of the following formula (7), for example, phenyl Grignard reagent and 4-dimethylaminophenyl Grignard reagent to form a sulfonium salt of formula (5a) having two tert-butoxyphenyl groups and possessing a chloride or bromide ion and thereafter, effecting anion exchange as mentioned above.

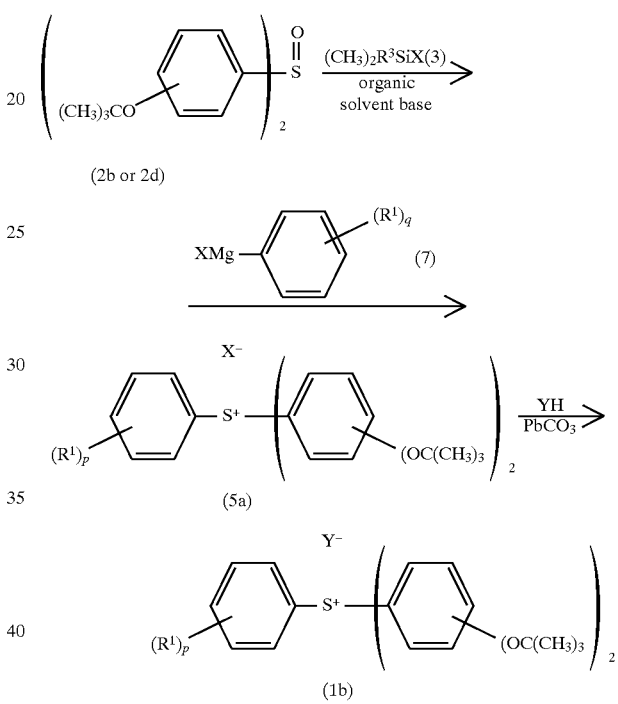

In the formulae, $R^1$, $R^3$, Y, X, p, and q are as defined above.

As seen from the above-mentioned reaction schemes, acid labile groups and various functional substituent groups can be introduced by changing the combination of a diphenyl sulfoxide derivative and an aryl Grignard reagent. For example, sulfonium salts having three phenyl groups each having an acid labile group can be synthesized in various combinations embracing a sulfonium salt having all the substituents at the 4-position of phenyl groups, a sulfonium salt having all the substituents at the 3-position, a sulfonium salt having two substituents at the 4-position and one substituent at the 3-position, and a sulfonium salt having one substituent at the 4-position and two substituents at the 3-position.

It is noted that where a sulfoxide having tert-butoxy groups at 2 and 2'-positions like bis(2,4-di-tert-butoxyphenyl) sulfoxide is used as the sulfoxide of formula (2), a sulfonium salt cannot be formed because of steric hindrance. This is also true where a sulfoxide having tetrahydropyranyloxy groups at 2 and 2'-positions is used. It is noted that a sulfonium salt having only one 2-substituted phenyl group can be synthesized when a reagent of formula (7) has a tert-butoxy group at the 2-position.

In a conventional method for synthesizing a sulfonium salt or sulfoxide compound through reaction of phenol or anisole with thionyl chloride, there can be formed either an ortho- or para-substituted compound depending on a particular reagent used since the phenol has two active sites at the ortho and para-positions. Instead, a meta-substituted compound cannot be obtained. In this reaction, synthesis starting with a compound having an acid labile group such as tert-butoxyphenyl is difficult since hydrogen chloride gas is given off in the reaction system. In contrast, the method using a Grignard reagent according to the invention is advantageous in that only a meta-substituted compound is obtained in a quantitative manner and decomposition of an acid labile group does not proceed because only an inorganic salt such as magnesium chloride is formed instead of hydrogen chloride gas.

In the synthesis of conventional sulfonium salts which generate strong acids such as sulfonium trifluoromethanesulfonate according to prior art techniques, sulfoxides, Grignard reagents, and trialkylsilylsulfonates (e.g., trialkylsilyltrifluoromethanesulfonates) are used as in the above-mentioned reaction, to thereby introduce an anion such as trifluoromethanesulfonate. If the prior art process is applied to the synthesis of a novel sulfonium salt of the invention, a substituted alkyl- or aryl-sulfonate anion can be introduced, but quantitative anion introduction is difficult at low acid strength. In this regard, the above-mentioned reaction process of the present invention which is to remove the chloride or bromide ion as lead chloride or lead bromide is successful in effecting anion exchange in a substantially quantitative manner.

Although the above-mentioned synthesis process uses a tert-butoxyphenyl Grignard reagent as a starting reactant for the sulfoxide and the sulfonium salt, it is also possible to synthesize a sulfonium salt of formula (1) by using a Grignard reagent prepared by protecting the hydroxyl group of a halogenated phenol with a protective group inert to the Grignard reagent and decomposable with an acid, for example, tetrahydropyranyl, tetrahydrofuranyl, and ethoxyethyl groups and reacting it with magnesium.

In the above-mentioned synthesis reaction of the sulfonium salts, it is preferred to mix 1 mol of the sulfoxide of formula (2) with 1 to 5 mol, especially 2 to 3 mol of the trialkylsilyl chloride or bromide of formula (3) and to add 1 to 5 mol, especially 2 to 3 mol of the Grignard reagent of formula (4) or (8) per mol of the sulfoxide of formula (2). These reactions are desirably effected in an organic solvent such as THF and methylene chloride in the presence of an organic base such as triethylamine and pyridine for preventing the decomposition of tert-butoxy group due to traces of acidic impurities in the trialkylsilyl halide of formula (3). Reaction conditions are not restrictive although a reaction temperature of 0° to 10° C. is preferred.

In carrying out anion exchange on the sulfonium salt having a chloride or bromide ion obtained under the above-mentioned reaction conditions, it is desirable, though not critical, to add 1.0 to 1.5 mol of the substituted alkyl or arylsulfonic acid of formula (6) and 0.5 to 1.5 mol of lead carbonate per mol of the sulfonium salt of formula (5) and effecting reaction in an organic solvent such as methanol at a temperature of 0° to 50° C. for 30 minutes to 2 hours. In this regard, if the proportion of the substituted alkyl or arylsulfonic acid of formula (6) or the reaction temperature is too high, there is a possibility that decomposition reaction of a tert-butoxyphenyl group or acid labile group take place.

According to the present invention, a novel sulfonium salt of formula (1) having a desired acid labile group and a substituted alkyl or arylsulfonate anion can be obtained by further decomposing the tert-butoxy group of the sulfonium salt of formula (1a) or (1b) with the substituted alkyl or arylsulfonic acid of formula (6) and substituting an acid labile group such as tert-butoxycarbonyl, tert-butoxycarbonylmethyl, trialkylsilyl, tetrahydropyranyl, tetrahydrofuranyl, ethoxyethyl, and methoxymethyl groups for the hydrogen atom of a phenolic-hydroxyl group in a conventional manner as shown below.

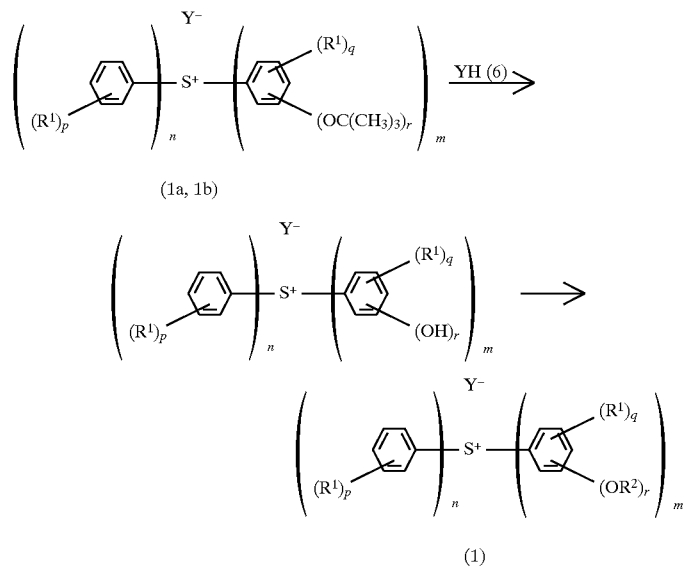

In the formulae, $R^1$, $R^2$, Y, n, m, p, q, and r are as defined above.

Synthesis of substituted alkylsulfonic acids can be done in accordance with R. K. Crossland, et al., J. Am. Chem. Soc., 93, 4217 (1971).

In a second aspect, the present invention provides a chemically amplified, positive working resist composition comprising the sulfonium salt of formula (1). The resist composition may be formulated as either a two component chemically amplified, positive resist composition (alkali soluble resin/photoacid generator/organic solvent) or a three component chemically amplified, positive resist composition (alkali soluble resin/photoacid generator/ dissolution rate inhibitor/organic solvent), with the three component system being preferred.

Typical embodiments of the resist composition of the invention are shown below.

Embodiment (i) is a chemically amplified positive resist composition comprising (A) an organic solvent,
(B) an alkali soluble resin,
(C) a dissolution rate inhibitor having an acid labile group,
(D) a sulfonium salt of formula (1), and
(E) a photoacid generator.

Embodiment (ii) is a chemically amplified positive resist composition comprising (A) an organic solvent,
(B) an alkali soluble resin,
(C) a dissolution rate inhibitor having an acid labile group,
(D) a sulfonium salt of formula (1), and
(F) an onium salt of the following general formula (8):

$$(R^4)_a MY' \qquad (8)$$

wherein $R^4$ is independently selected from substituted or unsubstituted aromatic groups, M is sulfonium or iodonium, Y' is a substituted or unsubstituted alkylsulfonate or arylsulfonate, and letter a is equal to 2 or 3.

Embodiment (iii) is a chemically amplified positive resist composition comprising (A) an organic solvent,
(B) an alkali soluble resin,
(C) a dissolution rate inhibitor having an acid labile group, and
(D) a sulfonium salt of formula (1).

Embodiment (iv) is a chemically amplified positive resist composition comprising (A) an organic solvent,
(B) an alkali soluble resin, and
(D) a sulfonium salt of formula (1).

Embodiment (v) is a chemically amplified positive resist composition comprising (A) an organic solvent,
(B) an alkali soluble resin,
(D) a sulfonium salt of formula (1), and
(E) a photoacid generator.

Examples of organic solvent (A) include ketones such as cyclohexanone and methyl amyl ketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate and ethyl 3-ethoxypropionate, alone or in admixture of two or more.

Examples of alkali soluble resin (B) as the base resin include polyhydroxystyrene and derivatives thereof. Preferred are those polyhydroxystyrene derivatives wherein hydrogen atoms of some OH groups of polyhydroxystyrene are replaced by acid labile groups and hydroxystyrene copolymers. In the former, examples of the acid labile group used therein include substituents of tert-butyl derivatives such as tert-butyl, tert-butoxycarbonyl, and tert-butoxycarbonylmethyl groups; normal or branched chain acetal groups such as 1-ethoxyethyl, 1-propoxyethyl, 1-n-butoxyethyl, 1-isobutoxyethyl, 1-tert-butoxyethyl, and 1-tert-amyloxyethyl groups; and cyclic acetal groups such as tetrahydrofuranyl, tetrahydropyranyl, and 2-methoxytetrahydropyranyl groups. These acid labile groups may be used alone or in admixture of two or more at the same time. The polyhydroxystyrene derivatives should preferably have a weight average molecular weight of about 3,000 to about 100,000. Film formability and resolution would be poor with Mw of less than 3,000 whereas resolution would be poor with Mw of more than 100,000. Included in the hydroxystyrene copolymers are copolymers of hydroxystyrene and styrene, copolymers of hydroxystyrene and tert-butyl acrylate, copolymers of hydroxystyrene and tert-butyl methacrylate, copolymers of hydroxystyrene and maleic anhydride, and copolymers of hydroxystyrene and di-tert-butyl maleate.

According to the invention, the sulfonium salt of formula (1) is blended as photoacid generator (D). If necessary, a mixture of sulfonium salts of formula (1) having different acid labile groups or different alkyl or aryl sulfonate anions may be used. Also if necessary, another photoacid generator may be blended as component (E) in addition to the sulfonium salt of formula (1). The other photoacid generators which can be used as component (E) include onium salts, oxime sulfonic acid derivatives, 2,6-dinitrobenzylsulfonate derivatives, diazonaphthoquinone sulfonate derivatives, 2,4-bistrichloromethyl-6-aryl-1,3,5-triazine derivatives, aryl sulfonate ester derivatives, pyrogallol sulfonate ester derivatives, N-sulfonyloxyimide derivatives such as N-trifluoromethanesulfonyloxyphthalide and N-trifluoromethanesulfonyloxynaphthalide, α,α'-bisarylsulfonyl diazomethane derivatives, and α,α'-bisalkylsulfonyl diazomethane derivatives. Preferred are onium salts of the following general formula (8):

$$(R^4)_a MY' \qquad (8)$$

wherein $R^4$ is independently selected from substituted or unsubstituted aromatic groups, M is sulfonium or iodonium, Y' is a substituted or unsubstituted alkylsulfonate or arylsulfonate, and letter a is equal to 2 or 3. Exemplary aromatic groups represented by $R^4$ are a phenyl group and phenyl groups having an alkyl or alkoxy substituent as described for $R^1$ in formula (1).

Illustrative examples of the onium salt of formula (8) are given by the following iodonium and sulfonium salts.

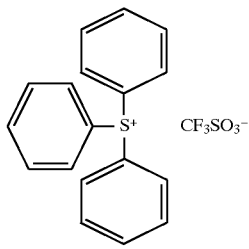

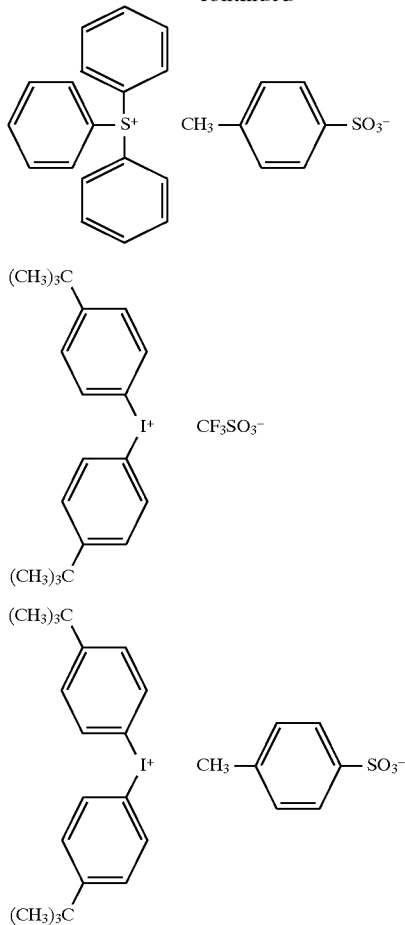

These photoacid generators may be used alone or in admixture of two or more.

Dissolution rate inhibitor (C) should have at least one group which is decomposable with an acid (acid labile group) in a molecule and may be either a low molecular weight compound or a polymer. Any of well-known dissolution rate inhibitors may be used. Exemplary low molecular weight compounds include bisphenol A derivatives and carbonate derivatives. Preferred are those bisphenol A derivatives wherein the hydrogen atom of a hydroxyl group of bisphenol A is replaced by tert-butyl derivative substituents such as tert-butyl, tert-butoxycarbonyl, and tert-butoxycarbonylmethyl groups; normal or branched chain acetal groups such as 1-ethoxyethyl, 1-propoxyethyl, 1-n-butoxyethyl, 1-isobutoxyethyl, 1-tert-butoxyethyl, and 1-tert-amyloxyethyl groups; and cyclic acetal groups such as tetrahydrofuranyl, tetrahydropyranyl, and 2-methoxytetrahydropyranyl groups. Also preferred are tert-butyl 4,4-bis(4-hydroxyphenyl)valerate derivatives wherein the hydrogen atom of the hydroxyl group is replaced by tert-butyl derivative substituents such as tert-butyl, tert-butoxycarbonyl, and tert-butoxycarbonylmethyl groups; normal or branched chain acetal groups such as 1-ethoxyethyl, 1-propoxyethyl, 1-n-butoxyethyl, 1-isobutoxyethyl, 1-tert-butoxyethyl, and 1-tert-amyloxyethyl groups; and cyclic acetal groups such as tetrahydrofuranyl and tetrahydropyranyl groups. These acid labile groups may be contained alone or in admixture of two or more.

Examples of the polymeric dissolution rate inhibitor include copolymers of p-butoxystyrene and t-butyl acrylate, and copolymers of p-butoxystyrene and maleic anhydride, with those copolymers having a weight average molecular weight of about 500 to about 10,000 being preferred.

Preferably the two-component resist composition is comprised of, in parts by weight, (A) about 150 to 700 parts, more preferably 250 to 500 parts of an organic solvent, and (B) about 70 to 90 parts, more preferably 75 to 85 parts of an alkali soluble resin. The three-component resist composition further contains (C) about 5 to 40 parts, more preferably 10 to 25 parts of a dissolution rate inhibitor having an acid labile group.

As component (D), about 0.5 to 15 parts, especially 2 to 8 parts of a sulfonium salt of formula (1) is preferably blended. With less than 0.5 part of the sulfonium salt, the amount of acid generated upon exposure would be too small to ensure sensitivity and resolution. With more than 15 parts of the sulfonium salt, a resist film would have low transmittance and resolution.

The other photoacid generator (E), if blended, is preferably used in amounts of about 0.5 to 15 parts, more preferably 2 to 8 parts.

The resist composition of the invention may further contain various additives, for example, carboxylic acid derivatives and nitrogenous compounds for improving PED stability, surfactants for facilitating coating, and light-absorbing agents for reducing irregular reflection from the substrate.

Exemplary carboxylic acid derivatives include 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, 4,4-bis(4-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. The carboxylic acid derivative is preferably blended in an amount of about 0.1 to 15 parts, especially about 1 to 10 parts in the resist composition of the invention.

Typical nitrogenous compounds are amine and amide compounds having a boiling point of 150° C. or higher. Examples include aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and triazines such as 2-(p-chlorophenyl)-4,6-trichloromethyl-s-triazine. Preferred among others are pyrrolidone, N-methylpyrrolidone, o-, m- and p-aminobenzoic acid, 1,2-, 1,3- and 1,4-phenylenediamine. The nitrogenous compound is preferably blended in an amount of about 0.05 to 4 parts, especially about 0.1 to 1 part in the resist composition of the invention.

Examples of the surfactant include perfluoroalkylpolyoxyethylene ethanols, fluorinated alkyl esters, perfluoroalkylamine oxides, and perfluoroalkyl EO addition products.

Examples of the light-absorbing agent include diaryl sulfoxides, diaryl sulfones, 9,10-dimethylanthracene, and 9-fluorenone.

With respect to the use of the resist composition of the invention and light exposure, any of well-known lithography techniques may be used. The resist composition of the invention is best suited for fine patterning using deep UV light of 254 to 193 nm and electron beams.

There has been described a novel sulfonium salt of formula (1) having an acid labile group introduced therein and serving as a photoacid generator. Due to the inclusion of an acid labile group, it affords an enhanced dissolution contrast between exposed and unexposed areas. Upon exposure, it generates a substituted alkyl or aryl-sulfonic acid which is weaker than conventionally generated acids such as trifluoromethanesulfonic acid. The weak acid is effective for minimizing side reaction during PEB step after exposure and the influence of deactivation of the generated acid by neutralization with a basic substance incoming from the resist film surface. Sensitivity is relatively high since the acid generated is not so weak as alkylsulfonic acids. Consequently, the sulfonium salt of formula (1) is useful as a component of a chemically amplified positive working resist composition adapted for fine patterning technique and having high resolution. Also, those sulfonium salts wherein an oxygen atom is introduced at the 3-position of a phenyl group to prevent the sulfonium salt from assuming a resonance structure between oxygen and sulfur atoms, that is, those sulfonium salts having an acid labile group introduced at the 3-position are effective for suppressing light absorption at about 250 nm equally to unsubstituted salts, resulting in a resist material having a high transmittance. The resist composition comprising a novel sulfonium salt of formula (1) as a photoacid generator is highly sensitive to actinic radiation such as deep UV, electron beams and X-rays, especially KrF excimer laser beams as a positive resist material, can be patterned by development with alkaline aqueous solution, and has high sensitivity, resolution and resistance to plasma etching with the resulting resist pattern having improved heat resistance.

EXAMPLE

Examples of the present invention are given below by way of illustration and not by way of limitation. The synthesis of novel sulfonium salts is described prior to Examples and Comparative Examples. All parts are by weight.

Synthesis Example 1

Synthesis of tris(4-tert-butoxyphenyl)sulfonium 2,2, 2-trifluoroethanesulfonate

A solution of 17.8 g (0.052 mol) of bis(4-tertbutoxyphenyl) sulfoxide in 52 g of THF was cooled on an ice bath. To the solution, 5.3 g (0.052 mol) of triethylamine was added and 14.1 g (0.13 mol) of trimethylsilyl chloride was dropwised at 0° to 10° C. Stirring was continued at 0 to 10° C. for 30 minutes. To this solution, a Grignard reagent which was conventionally prepared from 24.0 g (0.13 mol) of 4-tert-butoxychlorobenzene, 3.2 g (0.13 mol) of magnesium, and 40 g of THF was dropwised at 0° to 10° C. Stirring was continued at 0° to 10° C. for 30 minutes. 300 g of 20% ammonium chloride aqueous solution was added to the reaction mixture. To the organic layer was added 500 g of chloroform. The organic layer was washed twice with 200 g of water and the solvent was evaporated and residue was purifie by column chromatography (silica gel, eluent: chloroform/methanol), isolating 9.3 g (yield 35%) of tris(4-tert-butoxyphenyl)sulfonium chloride with 99% purity.

In 93 g of methanol was dissolved 9.3 g (0.018 mol) of tris(4-tert-butoxyphenyl)sulfonium chloride. 3.5 g (0.013 mol) of lead carbonate and 3.6 g (0.022 mol) of 2,2,2-trifluoroethanesulfonic acid were added to the solution, which was heated at 50° C. After cooling, the precipitate was filtered off and the filtrate was evaporated. 100 g of chloroform was added to the residue, the solution was washed with 100 g of water, and the solution was evaporated again, obtaining 8.2 g (two-steps yield 25%) of tris(4-tert-butoxyphenyl)sulfonium 2,2,2-trifluoroethanesulfonate with 97% purity.

The thus obtained tris(4-tert-butoxyphenyl)sulfonium 2,2, 2-trifluoroethanesulfonate was analyzed by nuclear magnetic resonance (NMR) spectroscopy, infrared (IR) spectroscopy, ultraviolet (UV) spectroscopy, and elemental analysis. The results are shown below.

$^1$H-NMR (CDCl$_3$, δ, ppm):

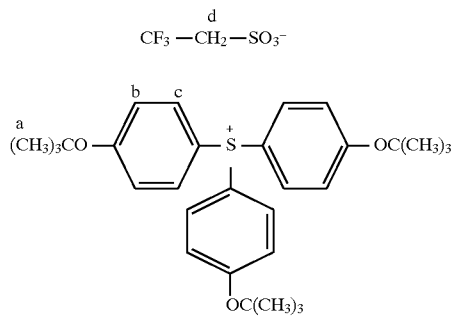

(a) 1.42 singlet 27H
(b) 7.15–7.19 doublet 6H
(c) 7.58–7.62 doublet 6H
(d) 3.53–3.64 quadruplet 2H IR:(cm$^1$) 2975, 1585, 1481, 1371, 1315, 1265, 1251, 1236, 1234, 1157, 1110, 1039, 896, 611

Elemental analysis for $C_{32}H_{41}O_6S_2F_3$ Calcd. (%) C: 59.8 H: 6.4 Found (%) C: 59.4 H: 6.3

Synthesis Example 2

Synthesis of (4-tert-butoxyphenyl) diphenylsulfonium 2,2,2-trifluoroethanesulfonate A solution of 20.2 g (0.10 mol) of diphenyl sulfoxide in 200 g of methylene chloride was cooled on an ice bath. To the solution, 5.3 g (0.052 mol) of triethylamine was added and 32.6 g (0.30 mol) of trimethylsilyl chloride was dropwised at 0° to 20° C. Stirring was continued at 0° to 10° C. for 15 minutes. To this solution, a Grignard reagent which was conventionally prepared from 55.4 g (0.30 mol) of 4-tert-butoxychlorobenzene, 7.3 g (0.30 mol) of magnesium, and 90 g of THF was dropwised at 0° to 10 ° C. Stirring was continued at 0° to 10° C. for 30 minutes. 500 g of 20% ammonium chloride aqueous solution was added to the reaction mixture. To the organic layer was added 1,000 g of chloroform. The organic layer was once washed with 200 g of water and the solvent was evaporated. The residue was purified by recrystalization, isolating 26.6 g (yield 72%) of (4-tert-butoxyphenyl)diphenylsulfonium chloride with 98% purity.

In 36 g of methanol was dissolved 3.3 g (0.009 mol) of (4-tert-butoxyphenyl)diphenylsulfonium chloride. 1.7 g (0.0063 mol) of lead carbonate and 1.6 g (0.010 mol) of 2,2,2-trifluoroethanesulfonic acid were added to the solution, which was heated at 40° C. After cooling, the precipitate was filtered off and the filtrate was evaporated.

100 g of chloroform was added to the residue, the solution was washed with 100 g of water, and evaporated again, obtaining 3.1 g (two-steps yield 50%) of (4-tert-butoxyphenyl)diphenylsulfonium 2,2,2-trifluoroethanesulfonate with 98% purity.

The thus obtained (4-tert-butoxyphenyl)diphenylsulfonium 2,2,2-trifluoroethanesulfonate was analyzed by NMR, IR, UV spectroscopy, and elemental analysis. The results are shown below.

$^1$H-NMR (CDCl$_3$, δ, ppm):

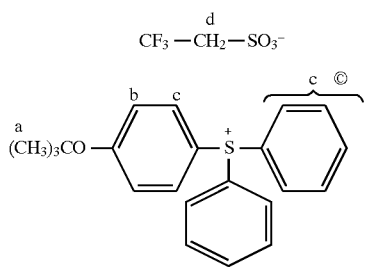

(a) 1.38 singlet 27H
(b) 7.13–7.17 doublet 2H
(c+c') 7.60'7.66 multiplet 12H
(d) 3.43–3.54 quadruplet 2H IR: (cm$^-$) 2977, 1585, 1490, 1486, 1446, 1332, 1311, 1253, 1251, 1228, 1160, 1143, 1072, 1056, 752, 622

Elemental analysis for C$_{24}$H$_{25}$O$_4$S$_2$F$_3$ Calcd. (%) C: 57.8 H: 5.05 Found (%) C: 57.5 H: 5.00

Synthesis Example 3

Reaction was carried out as in Synthesis Example 1 except that 4-fluorobenzenesulfonic acid was used instead of the 2,2,2-trifluoroethanesulfonic acid, obtaining tris(4-tert-butoxyphenyl)sulfonium 4-fluorobenzenesulfonate with 99% purity in a yield of 32%.

The thus obtained tris(4-tert-butoxyphenyl)sulfonium 4-fluorobenzenesulfonate was analyzed by NMR, IR, UV spectroscopy, and elemental analysis. The results are shown below.

$^1$H-NMR (CDCl$_3$, δ, ppm):

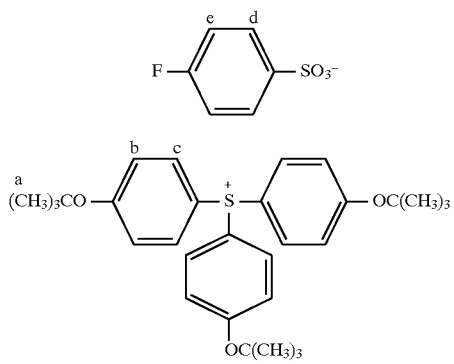

(a) 1.39 singlet 27H
(b) 7.11–7.14 doublet 6H
(c) 7.59–7.62 doublet 6H
(d) 6.85–6.91 triplet 2H
(e) 7.86–7.91 triplet 2H IR:(cm$^{-1}$) 2980, 1583, 1490, 1369, 1307, 1265, 1263, 1220, 1203, 1159, 1118, 1029, 894, 838, 682, 568

Elemental analysis for C$_{36}$H$_{43}$O$_6$S$_2$F$_1$ Calcd. (%) C: 66.0 H: 6.6 Found (%) C: 65.7 H: 6.3

Synthesis Example 4

Reaction was carried out as in Synthesis Example 2 except that pentafluorobenzenesulfonic acid was used instead of the 2,2,2-trifluoroethanesulfonic acid, obtaining (4-tert-butoxyphenyl)diphenylsulfonium pentafluorobenzenesulfonate with 98% purity in a yield of 36%.

The thus obtained (4-tert-butoxyphenyl)diphenylsulfonium pentafluorobenzenesulfonate was analyzed by NMR, IR, UV spectroscopy, and elemental analysis. The results are shown below.

$^1$H-NMR (CDCl$_3$, δ, ppm):

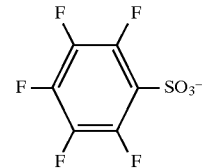

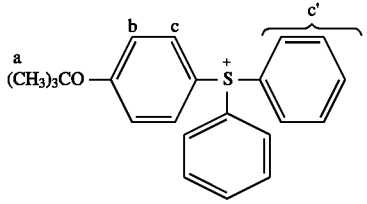

(a) 1.35 singlet 9H
(b) 7.11–7.14 doublet 2H
(c+c') 7.57–7.63 multiplet 12H

IR: (cm$^-$) 2980, 1648, 1585, 1531, 1527, 1488, 1444, 1395, 1245, 1226, 1160, 1097, 1058, 981, 752, 684, 659, 632

Elemental analysis for C$_{28}$H$_{23}$O$_4$S$_2$F$_5$ Calcd. (%) C: 57.7 H: 4.0 Found (%) C: 57.5 H: 3.9

Synthesis Example 5

Reaction was carried out as in Synthesis Example 1 except that phenyl Grignard reagent was used instead of the 4-tert-butoxyphenyl Grignard reagent, obtaining bis(4-tertbutoxyphenyl)phenylsulfonium 2,2,2-trifluoroethanesulfonate with 98% purity in a yield of 34%.

Synthesis Example 6

Reaction was carried out as in Synthesis Example 1 except that bis(4-dimethylaminophenyl) sulfoxide was used instead of the sulfoxide, obtaining (4-tert-butoxyphenyl)bis(4-dimethylaminophenyl)sulfonium 2,2,2-trifluoroethanesulfonate with 98% purity in a yield of 28%.

Synthesis Example 7

Reaction was carried out as in Synthesis Example 1 except that 4-dimethylaminophenyl Grignard reagent was used instead of the Grignard reagent, obtaining bis(4-tertbutoxyphenyl)(4-dimethylaminophenyl)sulfonium 2,2,2-trifluoroethanesulfonate with 98% purity in a yield of 32%.

Synthesis Examples 8–11

Reaction was carried out as in Synthesis Examples 1, 5 to 7 except that pentafluorobenzenesulfonic acid was used instead of the 2,2,2-trifluoroethanesulfonic acid, obtaining sulfonium salts having pentafluorobenzenesulfonate as a counter anion as shown below.

Synthesis Example 8 bis(4-tert-butoxyphenyl)phenylsulfonium pentafluorobenzenesulfonate, purity 98%, yield 35%

Synthesis Example 9

(4-tert-butoxyphenyl)bis(4-dimethylaminophenyl) sulfonium pentafluorobenzenesulfonate, purity 98%, yield 32%

Synthesis Example 10 bis(4-tert-butoxyphenyl)(4-dimethylaminophenyl) sulfonium pentafluorobenzenesulfonate, purity 99%, yield 31%

Synthesis Example 11 tris(4-tert-butoxyphenyl)sulfonium pentafluorobenzenesulfonate, purity 99%, yield 23%

Synthesis Example 12

Reaction was carried out as in Synthesis Example 1 except that 3-tert-butoxyphenyl Grignard reagent was used instead of the 4-tert-butoxyphenyl Grignard reagent and bis(3-tert-butoxyphenyl) sulfoxide was used instead of the bis(4-tert-butoxyphenyl) sulfoxide, obtaining tris(3-tertbutoxyphenyl)sulfonium 2,2,2-trifluoroethanesulfonate with 98% purity in a yield of 28%.

Synthesis Example 13

Reaction was carried out as in Synthesis Example 1 except that 4-dimethylaminophenyl Grignard reagent was used instead of the 4-tert-butoxyphenyl Grignard reagent and bis(3-tert-butoxyphenyl) sulfoxide was used instead of the bis(4-tert-butoxyphenyl) sulfoxide, obtaining bis(3-tertbutoxyphenyl)(4-dimethylaminophenyl)sulfonium 2,2,2-trifluoroethanesulfonate with 97% purity in a yield of 24%.

Synthesis Example 14

Reaction was carried out as in Synthesis Example 3 except that phenyl Grignard reagent was used instead of the 4-tert-butoxyphenyl Grignard reagent and bis(3-tert-butoxyphenyl) sulfoxide was used instead of the bis(4-tert-butoxyphenyl) sulfoxide, obtaining bis(3-tert-butoxyphenyl)phenylsulfonium 4-fluorobenzenesulfonate with 97% purity in a yield of 17%.

Synthesis Examples 15–19

The novel sulfonium salts having a tert-butoxy group obtained in Synthesis Examples 1 to 14 were treated in methanol or ethanol with the same sulfonic acid as the counter anion (e.g., 2,2,2-trifluoroethanesulfonate) for decomposing the protective group, to thereby form corresponding hydroxyphenylsulfonium salts in a substantially quantitative manner. Thereafter, by a conventional process using di-tert-butyl dicarbonate, tert-butyl chloroacetate, dihydropyrane, dihydrofuran or ethyl vinyl ether, there were synthesized sulfonium salts having a substituted alkyl- or aryl-sulfonate anion and an acid labile group as shown below.

Synthesis Example 15 bis(3-tert-butoxycarbonylmethyloxyphenyl) phenylsulfonium 2,2,2-trifluoroethanesulfonate, purity 99%, yield 14%

Synthesis Example 16

(4-tert-butoxycarbonyloxyphenyl)diphenylsulfonium pentafluorobenzenesulfonate, purity 98%, yield 20%

Synthesis Example 17 bis(4-(ethoxyethyl)oxyphenyl)(dimethylaminophenyl) sulfonium 2,2,2-trifluoroethanesulfonate, purity 98%, yield 20%

Synthesis Example 18 tris(4-(tetrahydrofuranyl)oxyphenyl)sulfonium pentafluorobenzenesulfonate, purity 97%, yield 20%

Synthesis Example 19 tris(3-(tetrahydropyranyl)oxyphenyl)sulfonium 2,2,2-trifluoroethanesulfonate, purity 97%, yield 17%

Examples 1–15 & Comparative Examples 1–5

Liquid resist compositions were prepared by dissolving a polyhydroxystyrene, a photoacid generator, and a dissolution rate inhibitor in a solvent in accordance with the formulation shown in Table 1.

The polyhydroxystyrene was selected from a polyhydroxystyrene derivative of the following formula Polym. 1 wherein the hydrogen atom of some hydroxyl groups is protected with a tert-butoxycarbonyl group, a polyhydroxystyrene derivative of the following formula Polym. 2 wherein the hydrogen atom of some hydroxyl groups is protected with a tetrahydrofuranyl group, and a polyhydroxystyrene derivative of the following formula Polym. 3 wherein the hydrogen atom of some hydroxyl groups is protected with a 1-ethoxyethyl group. The photoacid generator was selected from the onium salts of the formulae PAG. 1 to PAG. 5. The dissolution rate inhibitor was 2,2'-bis(4-tert-butoxycarbonyloxyphenyl)propane of the formula DRI. 1. The solvent was 1-ethoxy-2-propanol (abbreviated as EtOIPA) or a solvent mixture of ethyl lactate (85 wt %) and butyl acetate (15 wt %).

Each of the compositions was passed through a 0.2- $\mu$m Teflon® filter. It was then spin coated onto a silicon wafer to form a coating of 0.7 $\mu$m thick. With the silicon wafer rested on a hot plate at 100° C., the coating was pre-baked for 120 seconds.

The film was exposed to a pattern of light by means of an excimer laser stepper model NSR 2005EX (manufactured by Nikon K.K., numerical aperture NA=0.5), baked at 90° C. for 90 seconds, and developed with an aqueous solution of 2.38% tetramethylammonium hydroxide, obtaining a positive pattern.

The resulting resist patterns were evaluated as follows.

First, sensitivity (Eth value) was determined. Provided that the exposure dose with which the top and bottom of a 0.30- $\mu$m line-and-space pattern were resolved at 1:1 was the optimum dose (sensitivity Eop), the minimum line width of a line-and-space pattern which was recognized separate at this dose was the resolution of a test resist. The profile of the resist pattern resolved was observed under a scanning electron microscope.

The resist was further determined for PED stability by exposing at the optimum exposure dose, leaving the resist film to stand for a varying time, and baking (PEB) the film. The delay time was determined at which a change in the resist pattern configuration was observed, for example, the line pattern became a T-top profile or resolution became impossible. The longer the delay time, the better is the PED stability. It is noted that in Examples 14 and 15, a nitrogenous compound or carboxylic acid derivative was added as an additive for imparting PED stability.

The results are shown in Table 1.

TABLE 1

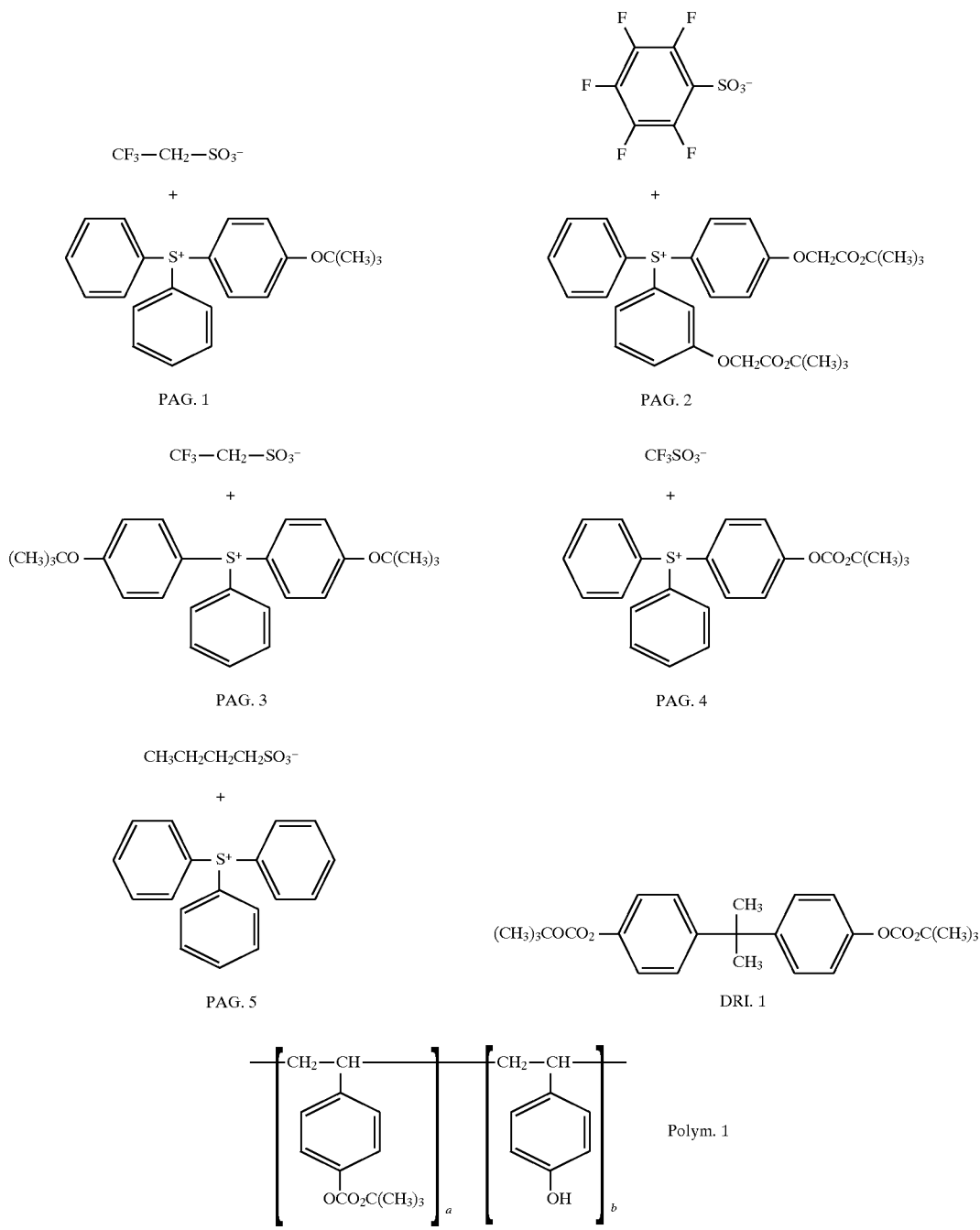

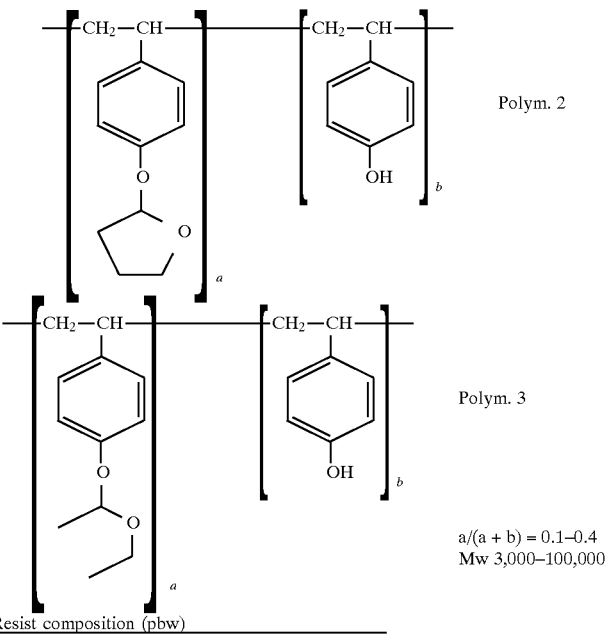

a/(a + b) = 0.1–0.4
Mw 3,000–100,000

Resist composition (pbw)

| | Alkali soluble resin | Photoacid generator | Dissolution rate inhibitor | Additive | Solvent | Sensitivity Eop (mJ/cm$^2$) | Resolution ($\mu$m) | Pattern profile | PED stability (min.) |
|---|---|---|---|---|---|---|---|---|---|
| E1 | Polym.1(80) | PAG.1(5) | DRI.1(20) | — | EtOIPA (500) | 14.0 | 0.28 | rectangular | 20 |
| E2 | Polym.1(40) Polym.2(40) | PAG.1(5) | DRI.1(20) | — | EtOIPA (500) | 11.0 | 0.26 | rectangular | 40 |
| E3 | Polym.1(40) Polym.3(40) | PAG.1(5) | DRI.1(20) | — | EtOIPA (500) | 8.0 | 0.24 | rectangular | 40 |
| E4 | Polym.1(40) Polym.3(40) | PAG.1(2) PAG.4(2) | DRI.1(20) | — | EtOIPA (500) | 6.0 | 0.24 | rectangular | 40 |
| E5 | Polym.2(75) | PAG.3(5) | — | — | EtOIPA (450) | 8.0 | 0.30 | rectangular | 100 |
| E6 | Polym.3(75) | PAG.2(5) | — | — | EtOIPA (450) | 7.0 | 0.30 | rectangular | 100 |
| E7 | Polym.2(70) | PAG.3(5) | DRI.1(20) | — | EtOIPA (500) | 8.0 | 0.24 | rectangular | 100 |
| E8 | Polym.3(70) | PAG.2(5) | DRI.1(20) | — | EtOIPA (500) | 8.0 | 0.24 | rectangular | 100 |
| E9 | Polym.2(70) | PAG.1(3) PAG.5(2) | DRI.1(20) | — | EtOIPA (500) | 6.0 | 0.24 | rectangular | 40 |
| E10 | Polym.1(40) Polym.2(40) | PAG.2(2) PAG.4(2) | DRI.1(20) | — | EtOIPA (450) | 6.0 | 0.24 | rectangular | 40 |
| E11 | Polym.1(40) Polym.3(40) | PAG.3(2) PAG.4(2) | DRI.1(20) | — | EtOIPA (500) | 7.0 | 0.24 | rectangular | 40 |
| E12 | Polym.1(40) Polym.2(40) | PAG.1(3) PAG.4(2) | DRI.1(20) | — | EtOIPA (500) | 6.0 | 0.24 | rectangular | 40 |
| E13 | Polym.1(40) Polym.3(40) | PAG.3(2) PAG.4(2) | DRI.1(20) | — | EtOIPA (500) | 6.0 | 0.24 | rectangular | 40 |
| E14 | Polym.1(40) Polym.3(40) | PAG.1(5) | DRI.1(20) | NMP(0.1) | EtOIPA (450) | 10.00 | 0.26 | rectangular | 100 |
| E15 | Polym.1(40) Polym.2(40) | PAG.1(5) | DRI.1(20) | BHVA(10) | EtOIPA (450) | 13.0 | 0.26 | somewhat forward taper | 60 |
| CE1 | Polym.1(75) | PAG.4(5) | DRI.1(20) | — | EtOIPA (500) | 4.0 | 0.28 | somewhat forward taper | ≦5 |
| CE2 | Polym.1(75) | PAG.5(5) | DRI.1(20) | — | EtOIPA (500) | 80.0 | 0.35 | forward taper | 30 |
| CE3 | Polym.2(75) | PAG.5(5) | DRI.1(20) | — | EtOIPA (500) | 55.0 | 0.32 | forward taper | 60 |
| CE4 | Polym.3(80) | PAG.4(6) | — | — | EtOIPA (500) | 50.0 | 0.32 | forward taper | 60 |
| CE5 | Polym.3(80) | PAG.4(6) | — | — | EtOIPA (500) | 3.0 | 0.30 | forward taper | ≦5 |

EtOIPA: 1-ethoxy-2-propanol
PGMEA: propylene glycol monomethyl ether acetate
EL/BA: a solvent mixture of ethyl lactate (85 wt %) and butyl acetate (15 wt %)
NMP: N-methylpyrrolidone
BHVA: 4,4-bis(4-hydroxyphenyl)valeric acid Japanese Patent Application No. 309849/1995 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A sulfonium salt having at least one acid labile group attached to a phenyl group in a molecule and an electron withdrawing group-substituted alkyl- or arylsulfonate and represented by the following general formula (1):

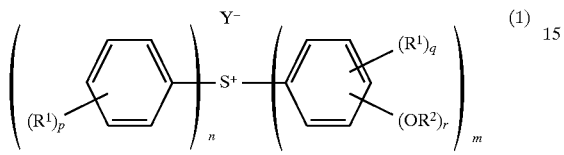

wherein $R^1$ is an alkyl, alkoxy or dialkylamino group, the groups represented by $R^1$ may be the same or different, $OR^2$ is an acid labile group, Y is a normal, branched or cyclic substituted alkylsulfonate having 2 to 20 carbon atoms or substituted arylsulfonate wherein the alkyl group of the alkylsulfonate has at least one hydrogen atom attached to a carbon atom at β-position or subsequent position replaced by an electron withdrawing group, and the aryl group of the arylsulfonate has at least one hydrogen atom of its benzene ring replaced by an electron withdrawing group, letter n is an integer of 0 to 2, m is an integer of 1 to 3, the sum of n and m is equal to 3, r is an integer of 1 to 5, p is an integer of 0 to 5, q is an integer of 0 to 4, the sum of q and r is an integer of 1 to 5.

2. A chemically amplified positive resist composition comprising a sulfonium salt of formula (1) as set forth in claim 1.

3. A chemically amplified positive resist composition comprising (A) an organic solvent, (B) an alkali soluble resin, (C) a dissolution rate inhibitor having an acid labile group, (D) a sulfonium salt of formula (1) as set forth in claim 1, and (E) a photoacid generator.

4. A chemically amplified positive resist composition comprising (A) an organic solvent, (B) an alkali soluble resin, (D) a sulfonium salt of formula (1) as set forth in claim 1, and (E) a photoacid generator.

5. The composition of claim 3 wherein said alkali soluble resin (B) is a polyhydroxystyrene in which hydrogen atoms of some hydroxyl groups are replaced by acid labile groups and which has a weight average molecular weight of about 3,000 to about 100,000.

6. The composition of claim 4 wherein said alkali soluble resin (B) is a polyhydroxystyrene in which hydrogen atoms of some hydroxyl groups are replaced by acid labile groups and which has a weight average molecular weight of about 3,000 to about 100,000.

7. A sulfonium salt as in claim 1, wherein n=2 and m=1.

8. A sulfonium salt as in claim 1, wherein Y is substituted arylsulphonate.

9. A sulfonium salt as in claim 1, wherein Y is selected from the group consisting of 2,2,2-trifluoroethyl-sulfonate; 1H,1H-heptafluoro-1-butylsulfonate; 1H,1H-perfluoro-1-heptylsulfonate; 1H,1H-perfluoro-1-dodecylsulfonate; 2-nitroethanesulfonate; 1-nitropropane-2-sulfonate; 2-nitropropane-1-sulfonate; penta-fluorobenzenesulfonate; 4-fluorobenzenesulfonate; 2-, 3- or 4-nitrobenzenesulfonate; and 2,4-dinitrobenzenesulfonate.

* * * * *